United States Patent
Salsarulo et al.

(10) Patent No.: US 6,221,853 B1
(45) Date of Patent: Apr. 24, 2001

(54) LACTULOSE-BASED ANHYDROUS COMPOSITION

(76) Inventors: Odette M. Salsarulo; Gerard Salsarulo, both of 14, rue de la Belle Feuille, 92100 Boulogne-Billancourt (FR)

( * ) Notice: Subject to any disclaimer, the term of this patent is extended or adjusted under 35 U.S.C. 154(b) by 0 days.

(21) Appl. No.: 09/176,213

(22) Filed: Oct. 21, 1998

(30) Foreign Application Priority Data

Oct. 21, 1997 (FR) .................................................. 97 13186

(51) Int. Cl.⁷ ........................ A61K 31/715; A61K 47/00
(52) U.S. Cl. ............................ 514/53; 514/964; 514/965; 424/439
(58) Field of Search ............................ 424/439; 514/964, 514/965, 53

(56) References Cited

FOREIGN PATENT DOCUMENTS

| 0 486 353 A1 | 10/1991 | (EP) . | |
| 0 486 353 A1 | * 5/1992 | (EP) .............................. | A61K/31/70 |
| 543 309 | 2/1942 | (GB) . | |
| WO 95/22976 | 8/1995 | (WO) . | |

OTHER PUBLICATIONS

Yamauchi, Akira, Laxatives Containg Lactose & Microorganisms, AN 1986:230506 CAPLUS, See Abstract and Citation.*

Bolhuis et al, Evaluation of Anhydrous Alpha Lactose, AN 1985:547101 CAPLUS , See Abstract and Citation.*

* cited by examiner

Primary Examiner—Russell Travers
(74) Attorney, Agent, or Firm—Leonard R. Svensson; Birch, Stewart, Kolasch & Birch, LLP

(57) ABSTRACT

The invention relates to a lactulose-based medicinal product, characterized by the incorporation of anhydrous lactulose into a coating vehicle, which is also anhydrous, consisting of a mixture of pharmaceutically acceptable purified paraffinic hydrocarbons, this vehicle having a melting point of about 37° C.±4° C.

It is, in particular, dosed so as to allow the administration of 3 to 5 g per day to an adult, in particular in a single dosage intake.

14 Claims, No Drawings

LACTULOSE-BASED ANHYDROUS COMPOSITION

Lactulose is a recognized laxative which acts, on the basis of its osmotic power, in the intestine.

Pharmaceutically, lactulose is usually:

either in the form of a 50% solution or in pure powdered form, but, in this case, patients ingest it with water.

In these presentations, the active oral doses of lactulose are high, ranging from 10 to 30 grams/day (for an adult) in terms of pure powder value (which often makes it necessary to take several doses during the day). Oral administration is not without problems relating to the tolerance of the product by the body. It is liable to result in undesirable side effects, such as flatulence or a bloated feeling.

The aim of the invention is to provide a pharmaceutical composition which makes it possible largely to overcome the abovementioned drawback, i.e. which allows the daily administration of lower doses of lactulose while at the same time retaining an equivalent laxative activity.

The composition or pharmaceutical form described in French patent No. 9013619/2688706, characterized by the incorporation of anhydrous lactulose into a pharmaceutically acceptable vehicle for the oral route, which is also anhydrous, having in particular a melting point of between 45° C. and 60° C. and consisting of a mixture of purified paraffinic hydrocarbons, already largely overcame the abovementioned drawbacks.

Indeed, not only can these lactulose-based pharmaceutical compositions be ingested without water, and thus be taken as they are by patients, but also the clinical working daily doses were able to be lowered to 5 to 10 grams of lactulose per day for an adult.

The present invention is an improvement of the composition described in the French patent identified above. It results from the twofold discovery that:

the efficacy due to the osmotic pressure exerted during absorption of the medicinal product of the above patent was not affected by the use, for the coating vehicle, of a mixture of paraffinic hydrocarbons, usually paraffinic carbon distillates containing liquid paraffin, but having a lower melting point, in particular of about 37° C. instead of 45 to 60° C., and the clinical working dosage of lactulose which can be administered daily under these conditions was able to be reduced even further, resulting in an even greater reduction in the side effects (flatulence or a bloated feeling) of lactulose when it is used at high doses.

The composition according to the invention which contains anhydrous lactulose coated in a vehicle which is also anhydrous consisting of a mixture of pharmaceutically acceptable purified hydrocarbons, is thus characterized in that the vehicle has a melting point of about 37° C.±4° C., thus equal to, or in any case close to, body temperature.

It should be noted that the abovementioned melting point, of about 37° C., corresponds to a capillary melting point which can be measured with a variability of ±5% by carrying out the technique described in the French Pharmacopoeia, 10th edition, 1983, V.611.

According to an additional preferred characteristic of the invention, the anhydrous lactulose used in these compositions is micronized, the particle sizes advantageously being between 75 and 150 $\mu$m. The incorporation of anhydrous lactulose thus micronized into the vehicle, in particular the coating of its particles in the vehicle, results in greater dispersion of the lactulose in the composition and an additional increase in its osmotic pressure.

The result of this is that the clinical working doses of lactulose which can be administered to an adult in this new form can be lowered even further, and in particular can be reduced to 3.5 to 5 grams per day, instead of the daily doses which still required the use of the compositions of the above paten: 5 to 10 grams of lactulose per day for an adult.

It goes without saying that the composition thus obtained does not necessarily represent the final pharmaceutical presentation as will be given to patients. This presentation can also contain other excipients provided that the anhydrous nature of the lactulose, which is the basis of its osmotic pressure, is maintained, and as long as the final composition does indeed contain the abovementioned working doses of lactulose.

As in the case of the above patent, the hydrocarbon-based vehicle advantageously consists of anhydrous distillates of paraffinic carbons, refined to a level which makes them completely harmless and, if need be, selected such that this mixture has a melting point of about 37° C., by optional and complementary addition of pharmacopoeia-grade liquid paraffin. The preferred vehicle thus consists of a mixture of paraffinic carbon distillates containing liquid paraffin, it being understood that the relative proportions of these constituents are to be selected by a person skilled in the art on the basis of the melting point chosen, of about 37° C. By way of non-limiting example, it will be indicated that the proportion of liquid paraffin will, as a result, often be within a proportion ranging from ¼ to ¾ of the weight of the composition. It goes without saying that the liquid paraffin can even be left out if the mixture of paraffinic carbon distillates itself already has a melting point of about 37° C.

Three compositions which satisfy the conditions of the invention are given below, as examples, it nevertheless being understood that they should in no way be considered as being limiting in nature.

The proportion of the coating (paraffinic carbons and liquid paraffin) is about 1 to 2 times the amount of lactulose. Thus, the proportion of lactulose relative to the entire composition is advantageously from about 30 to 45% by weight of the total composition, and, for example, of about 3.5 g of lactulose per 6.5 g of hydrocarbons.

The use of the composition according to the invention is naturally accompanied by the advantages already mentioned with regard to the invention described in the above patent, but to an even greater beneficial degree since it allows, for the same efficacy, an additional reduction in dosage, in particular by virtue of the additional reduction of the effective doses of lactulose, to 3 to 5 grams per day instead of the 5 to 10 grams per day required for the composition of the prior patent.

Advantageously, the composition is in a pharmaceutical form such that it allows the administration of effective daily doses of about 3.5 to 5 grams of lactulose per day, preferably in a single dosage intake. At this reduced dose, the tolerance is greatly improved.

EXAMPLE 1 (for 100 g)

| | |
|---|---|
| Lactulose | 40 g |
| Petroleum jelly* | 30 g |
| Liquid paraffin | 30 g |

*The characteristics of this paraffinic carbon featured in the French pharmacopoeia, 10th edition, of petroleum jellies were as follows:

| | |
|---|---|
| Drop point (Mettler method FP5/53) | 52° C. |

-continued

| | |
|---|---|
| Penetration index (cone 25/150, units $10^{-4}$ m) | 120 |
| Density at 20° C. | 0.85 |

EXAMPLE 2 (for 100 g)

| | |
|---|---|
| Lactulose | 35 g |
| Petroleum jelly* | 21 g |
| Liquid paraffin | 42 g |
| Flavouring | 2 g |
| *The characteristics of this paraffinic carbon featured in the French pharmacopoeia, 10th edition, for the petroleum jellies were as follows: | |
| Drop point | 59° C. |
| Penetration index | 75 |
| Density at 20° C. | 0.86 |

EXAMPLE 3 (for 100 g)

| | |
|---|---|
| Lactulose | 35 g |
| Specific paraffinic mixture* | 64 g |
| Flavouring | 1 g |
| *Paraffinic mixture corresponding to a distillate provided at our request by the company CECA, this product being derived from a paraffinic hydrocarbon fraction consisting of paraffinic waxes, petroleum jellies and liquid paraffin, and having the following characteristics: | |
| Drop point | 38° C. |
| Penetration index | 180 |
| Consistency | pasty |

What is claimed is:

1. A laxative composition having a reduced amount of lactulose with a clinical working dose of 5 or less grams per day comprising anhydrous lactulose incorporated into an anhydrous coating vehicle, said coating vehicle comprising a mixture of pharmaceutically acceptable purified paraffinic hydrocarbons, and said vehicle having a melting point of about 37° C.±4° C. and wherein said lactulose comprises micronized particles of 75 to 150 micrometers (microns).

2. The composition according to claim 1 wherein the particles are dispersed and coated in the anhydrous vehicle.

3. The composition according to claim 1, wherein the proportion of lactulose relative to the entire composition is from abut 30 to 45% by weight of the total composition.

4. The composition according to claim 1, wherein the paraffinic hydrocarbon content equal is 1 to 2 times the lactulose content.

5. The composition according to claim 4, wherein the composition comprises about 3.5 grams of lactulose for about 6.5 grams of pharmaceutically acceptable paraffinic hydrocarbons.

6. Composition according to claim 3, characterized in that it allows the administration of an effective dose of lactulose in a proportion of 3.5 to 5 grams per day to adults.

7. Anhydrous laxative medicinal product which can be ingested without water, for oral administration, containing a composition according to claim 1.

8. Medicinal product according to claim 7, characterized in that it is in a pharmaceutical form which allows administration of an effective dose in a proportion of 3 to 5 g of lactulose per day.

9. Medicinal product according to claim 7, characterized in that it is in a form which allows administration at the abovementioned dose in a single daily dosage intake.

10. A laxative composition having a reduced amount of lactulose with a clinical working dose of 5 or less grams per day comprising anhydrous lactulose incorporated into an anhydrous coating vehicle, said coating vehicle comprising a mixture of pharmaceutically acceptable purified paraffinic hydrocarbons, and said vehicle having a melting point of about 37° C. and wherein said lactulose is in the form of micronized particles of 75 to 150 micrometers (microns).

11. The composition according to claim 10, wherein said particles are dispersed and coated in said anhydrous vehicle.

12. The composition according to claim 11, wherein the proportion of lactulose relative to the entire composition is from about 30 to 45% by weight of the total composition.

13. The composition according to claim 11, wherein said composition has a paraffinic hydrocarbon content of 1 to 2 times the lactulose content.

14. The composition according to claim 11, wherein said composition comprises about 3.5 grams of lactulose for about 6.5 grams of said paraffinic hydrocarbons.

* * * * *